United States Patent [19]
Schmidt et al.

[11] 3,993,689
[45] Nov. 23, 1976

[54] β-ACYLOXY-CROTONIC ACID AMIDE-N-SULFOHALIDES AND A PROCESS FOR THEIR PREPARATION

[75] Inventors: Erwin Schmidt, Kelkheim, Taunus; Karl Clauss, Rossert, Taunus; Hartmut Pietsch, Hofheim, Taunus; Harald Jensen, Frankfurt am Main, all of Germany

[73] Assignee: Hoechst Aktiengesellschaft, Frankfurt am Main, Germany

[22] Filed: July 16, 1975

[21] Appl. No.: 596,218

[30] Foreign Application Priority Data
July 18, 1974 Germany............................ 2434547

[52] U.S. Cl............................. 260/490; 260/239 A; 260/243 R; 260/543 R; 260/543 F
[51] Int. Cl.$^2$........................................ C07C 161/00
[58] Field of Search................................... 260/490

[56] References Cited
OTHER PUBLICATIONS
Chem. Abstracts, 54:19489f–h.

*Primary Examiner*—Vivian Garner
*Attorney, Agent, or Firm*—Curtis, Morris & Safford

[57] ABSTRACT
Compounds of the formula

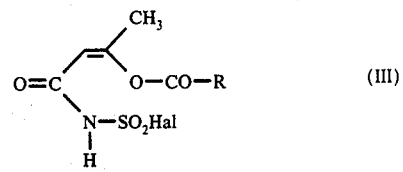

in which R represents an alkyl radical having from 1 to 4 carbon atoms and Hal stands for fluorine or chlorine are prepared by reacting at a temperature of from −40° to +20° C an i-propenylalkanoic acid ester of the formula

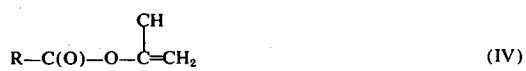

with an isocyanate of the formula

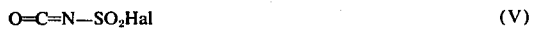

in which R and Hal have the same meaning as above, and isolating the compound of formula III.

9 Claims, No Drawings

β-ACYLOXY-CROTONIC ACID AMIDE-N-SULFOHALIDES AND A PROCESS FOR THEIR PREPARATION

This invention relates to β-acyloxy-crotonic acid amide-N-sulfohalides, a process for their preparation and their transformation into sweeteners.

U.S. Pat. No. 3,689,486 is concerned with a process for the preparation of oxathiazinone derivatives which comprises reacting a β-ketocarboxylic acid amide-N-sulfonyl derivative with a base.

6-Methyl-3,4-dihydro-1,2,3-oxathiazin-4-one-2,2-dioxide of the following formula I is an acid which is distinguished as such and especially in the form of its neutral potassium, sodium and calcium salts by an intensive sweet taste and can, therefore, be considered a new sweetener low in calories.

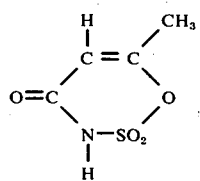
(I)

The most simple synthesis of this compound is the addition of chloro- or fluorosulfonyl isocyanate on acetone to obtain aceto-acetamide-N-sulfohalides of formula II

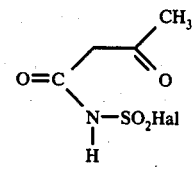
(II)

which can then be transformed into the 6-methyl-3,4-dihydro-1,2,3-oxathiazin-4-one-2,2-dioxide or the salts thereof by the action of bases and with splitting off of hydrogen halide. This synthesis, however, which is very interesting because of the large amounts of acetone produced in industry, gives a yield of 13% only according to the aforesaid specification.

It has now been found that the enol esters of acetoacetamide-N-sulfohalides of the formula III

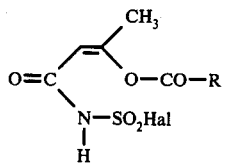
(III)

i.e. β-acyloxy-crotonic acid amide-N-sulfohalides, in which R represents an alkyl group can be prepared in a good yield by reacting the corresponding enol esters of acetone, that is the i-propenyl esters, with halosulfonyl isocyanates.

The enol esters of formula III can be transformed into the compound of formula I like the free acetoacetamide-N-sulfohalides of formula II in a manner analogous to that described in the above specification or in South African Pat. No. 74/3234.

It is, therefore, the object of the present invention to provide β-acyloxy-crotonic acid amide-N-sulfohalides of the formula III in which R represents an alkyl radical having from 1 to 4 carbon atoms and Hal is fluorine or chlorine, and a process for the preparation of the said compounds, which comprises reacting at a temperature of from −40° to +20° C i-propenyl-alkanoic acid esters of the formula IV

with isocyanates of the formula V

in which formulae R and Hal have the aforesaid meaning.

The reaction is preferably carried out in an inert aprotic solvent or diluent, for example aliphatic and aromatic hydrocarbons such as pentane, hexane, i-octane, cyclohexane, light or heavy gasoline, benzene, toluene, xylene; halohydrocarbons such as methylene chloride, chloroform, carbon tetrachloride, tetrachloroethane, chlorobenzene, trifluoro-chloroethane, trichlorofluoromethane; carboxylic acid esters such as methyl acetate, ethyl acetate, butyl acetate, ethylene diacetate, methyl glycol acetate, phenyl acetate, i-propyl benzoate, or an excess of the i-propenyl ester used; nitriles such as acetonitrile and propionitrile; and ethers such as anisole and phenetole. Especially good results are obtained with low molecular weight aliphatic ethers commonly used as solvents in industry, for example dimethyl ether, diethyl ether, di-i-propyl ether, dibutyl ether, ethylene glycol dimethyl ether, dioxane, tetrahydrofurane, which can be readily removed from the reaction products even at relatively low temperatures. Inorganic aprotic solvents are also suitable, for example liquid sulfur dioxide.

The amount of solvent to be used is not critical and depends on the practical requirements in each case. In general, about 0.5 to 20 times the amount by weight, calculated on the mixture of the reaction components, is used. Smaller and larger amounts are likewise possible, the upper limit depending on economical considerations.

The reaction components IV and V are generally used in approximately stoichiometric amounts, an excess of up to 10% of either one being possible. To avoid secondary reactions it is expedient, however, to carry out the reaction under conditions such that the halosulfonyl isocyanate is not present in excess in the reaction mixture. It proved advantageous to add the isocyanate to the propenyl ester or to introduce into the reaction vessel dosed quantities of isocyanate and propenyl ester, optionally dissolved in a solvent, either uniformly or with a slight excess of the propenyl ester. Preferred reaction components are i-propenyl acetate and fluorosulfonyl isocyanate or chlorosulfonyl isocyanate.

The reaction is generally carried out a temperature in the range of from −40° to +20° C, preferably −30° to +10° C. At lower temperatures the reaction proceeds too slow while at higher temperatures the proportion of secondary products increases. The reaction is preferably carried out at a temperature in the range of from −20° to 0° C. When the reaction is terminated the reaction product III is isolated in known manner, for example by filtration, optionally after concentration by evaporation of the solvent, or by distilling off the solvent.

The compound of formula III can then be transformed into compound I by cyclization with splitting off of acyl halide at a temperature of from 50° to 150° C.

By splitting off the ester bond by means of water or hydrogen chloride they can also be transformed into the corresponding acetoacetamide-N-sulfohalides. In the case of the sulfofluoride the ester bond can be readily split by means of a small but at least the stoichiometric amount of water. Because of the sensitivity of the sulfochloride group splitting with HCl is preferred in the case of the N-sulfochloride compound.

The acetoacetamide-N-sulfohalides can be reacted according to the processes disclosed in the above specifications to yield 6-methyl-3,4-dihydro-1,2,3-oxathiazin-4-one-2,2-dioxide I or the salts thereof.

According to a preferred embodiment the enol ester III in which Hal is fluorine is reacted in one stage with an inorganic base, for example KOH or NaOH, whereby the corresponding salt of compound I is directly obtained.

Owing to the fact that the salts of compound I with inorganic cations, above all the alkali metal salts, more particularly the potassium salt, are sparingly soluble in alcohols, the cyclization to the 6-methyl-3,4-dihydro-1,2,3-oxathiazin-4-one-2,2-dioxide can be brought about in an especially simple and advantageous manner in an alcohol, for example methanol, ethanol, isopropanol, and the like, or mixtures thereof containing less than 50% by weight of water, preferably less than 20% by weight of water, with the addition of inorganic bases. The oxathiazinone (I) can be obtained from the alcoholic solution practically quantitatively in the form of a salt of the inorganic base used and from the salt the free oxathiazinone can be prepared without difficulty in known manner. It proved particularly advantageous to add methanolic potassium hydroxide or potassium methylate solution in an amount of at least 2 moles KOH or potassium methylate per mole sulfofluoride, to the crude β-acetoxy-crotonic acid amide-N-sulfofluoride dissolved in methanol, acetonitrile, or an ether, for example di-isopropyl ether or tetrahydrofurane, or another aprotic solvent used for making the sulfofluoride. The potassium salt of 6-methyl-3,4-dihydro-1,2,3-oxathiazin-4-one-2,2-dioxide (I) formed in this reaction separates in the form of crystals which can be filtered off with suction, while the potassium fluoride formed essentially remains in solution so that it can be readily separated from the desired reaction product. Hence, the cyclization in methanolic potassium hydroxide solution is a preferred embodiment of the process of the invention wherein the oxathiazinone (I) obtained is substantially free of fluoride, which may be extremely important when the compound is used as sweetener.

For a possible further purification the crude potassium salt of the oxathiazinone can be recrystallized from boiling water, optionally with addition of coal and filtering aids and obtained in a pure state. An addition of calcium hydroxide effectively promotes the separation of traces of fluoride in the form of insoluble $CaF_2$, which can be readily separated from the solution.

The purity of the 6-methyl-3,4-dihydro-1,2,3-oxathiazin-4-one-2,2-dioxide and its salts can be controlled in simple manner by UV measurement in dilute solution since the oxathiazinone shows a strong absorption maximum with $\epsilon =$ about $1 . 10^4$ at $225 - 228$ nm.

It is also possible, of course, to react the sulfohalide (III) to obtain the oxathiazinone (I) directly in the reacted mixture without prior isolation of the halide.

The reaction of the present invention of i-propenylalkanoic acid esters with halosulfonyl iso-cyanates constitutes a progress in the art and offers an advantageous mode of synthesis to obtain the sweetener 6-methyl-3,4-dihydro-1,2,3-oxathiazin-4-one-2,2,-dioxide (I) and its nontoxic salts.

Moreover, the β-acyloxy-crotonic acid amide-N-sulfohalides of formula III are novel compounds of which the compound carrying a methyl radical as R and a fluorine or chlorine atom as Hal is preferred.

The reaction in accordance with the present invention is surprising since it has been disclosed in German Offenlegungsschrift No. 1,906,401 that carboxylic acid vinyl esters react with chlorosulfonyl isocyanate with formation of β-lactam-N-sulfofluorides, a reaction which also takes place when i-propenylbenzoate is reacted, but does obviously not happen or is left out in the case of i-propenyl-alkanoic acid esters.

The following examples illustrate the invention.

EXAMPLE 1

170 ml (283 g = 2 moles) chlorosulfonyl isocyanate were added dropwise at $-20°$ C over a period of 3 hours and while stirring to a solution of 200 g (2 moles) i-propenyl acetate in 500 ml di-isopropyl ether. After stirring for 24 hours at $-20°$ C the β-acetoxy-crotonic acid amide-N-sulfochloride started to separate in the form of crystals.

When crystallization was terminated the product was filtered off with suction on a deep temperature suction filter with the exclusion of humidity and the crystals were dried at 0° C under reduced pressure.

Yield 240 g (50% of theory).
Analysis:
$C_6H_8ClNO_5S$ m.w. 241.65: calc.: C 29.82%; H 3.34%; Cl 14.68%; N 5.80%; S 13.27%; found: C 29.5%; H 3.5%; Cl 14.4%; N 6.0%; S 13.4%
IR-spectrum $(CH_2Cl_2)$: 3.0 μ (NH); 5.63 μ (CO); 5.79 μ (CO); 6.02 μ (C=C)
NMR-spectrum $(CD_3CN)$: 2.1 ppm (doublet, allyl-$CH_3$); 2.2 ppm (singlet, acetyl-$CH_3$); 5.8 ppm (quartet, allyl-CH=).

COMPARATIVE EXAMPLE 1 a

A solution of 14.1 g (0.1 mole) chlorosulfonyl isocyanate in 10 ml di-isopropyl ether was added dropwise at $+5°$ C − $+10°$ C over a period of 30 minutes and while stirring to a solution of 19.4 g (0.12 mole) i-propenyl benzoate in 30 ml di-isopropyl ether. The separating crystals of 4-benzoyloxy-4-methyl-azetidinone-N-sulfochloride were filtered off with suction and dried at 0° C under reduced pressure.

Yield 24.6 g (86% of theory)
Analysis:
IR-spectrum $(CH_2Cl_2)$: 5.45 μ, 5.51 μ(β-lactam-CO); 5.81 μ(benzoyl-CO); 6.28 μ(aryl)
NMR-spectrum: 2.2 ppm (singlet, $CH_3$); 3.65 ppm (A-B-system, β-lactam-$CH_2$; 7.4-8.2 ppm (benzoyl).

COMPARATIVE EXAMPLE 1 b 12.5 g (0.1 mole) fluorosulfonyl isocyanate were added dropwise over a period of 30 minutes at $+10°$ C and while stirring to a solution of 25 g (0.17 mole)

i-propenyl benzoate in 30 ml di-isopropyl ether. The separating crystals of 4-benzoyloxy-4-methyl-azetidinone-N-sulfofluoride were filtered off with suction and dried under reduced pressure. The yield amounted to 17.8 g (62% of theory, calculated on the isocyanate used).

Analysis:

$C_{11}H_{10}FNO_5S$ m.w. 287.26: calc.: C 45.99%; H 3.51%; F 6.61%; N 4.88%; S 11.16%; found: C 46.0%; H 3.6%; F 6.5%; N 4.4%; S 11.2% molecular weight: 287 (mass spectrum)

IR-spectrum: 5.47 $\mu$, 5.51 CH ($\beta$-lactam-CO); 5.83 $\mu$(benzoyl-CO); 6.30 $\mu$ (aryl)

NMR-spectrum: 2.2 ppm (singlet, $CH_3$); 3.7 ppm (AB-system, $\beta$-lactam-$CH_2$); 7.4 – 8.2 ppm (benzoyl).

EXAMPLE 2

250 g (2 moles) fluorosulfonyl isocyanate were added dropwise at −20° C while stirring to a solution of 200 g (2 moles) i-propenyl acetate in 500 ml di-isopropyl ether. The mixture was kept at −20° C for 64 hours, the separating crystals were filtered off with suction at −50° C and dried under reduced pressure at 0° C. 300 g (67% of theory) of $\beta$-acetoxy-crotonic acid amide-N-sulfo-fluoride were obtained.

Analysis;

$C_6H_8FNO_5S$ m.w. 225.19: calc.: C 32.00%; H 3.58%; F 8.44%; N 6.22%; S 14.24%; found: C 32.0%; H 3.6%; F 8.2%; N 6.2%; S 14.4%

IR-spectrum ($CH_2Cl_2$): 3.1 $\mu$ (NH); 5.69 $\mu$ (CO); 5.89 $\mu$ (CO); 6.02 $\mu$ (C=C)

NMR-spectrum ($CD_3CN$): 2.1 ppm (doublet, allyl-$CH_3$); 2.3 ppm (singlet, acetyl-$CH_3$); 5.75 ppm (quartet, allyl-CH=).

When the stoichiometric amount of water was added to the solution of a sample of the $\beta$-acetoxy-crotonic acid amide-N-sulfofluoride in di-isopropyl ether, the sulfofluoride dissolved solved quickly and after concentration of the solution by evaporation the acetoacetamide-N-sulfofluoride separated in the form of crystals.

22.5 g of $\beta$-acetoxy-crotonic acid-sulfofluoride were added, while stirring and cooling, to 100 ml 4N methanolic potassium hydroxide solution. After a few minutes the potassium salt of 6-methyl-3,4-dihydro-1,2,3-oxathiazin-4-one-2,2-dioxide started to separate in the form of crystals. The yield amounted to 18 g (90% of theory).

The same result was obtained when the $\beta$-acetoxy-crotonic acid amide-N-sulfofluoride was added to the methanolic potassium hydroxide solution in the form of a solution in methanol, acetonitrile, or tetrahydrofurane.

EXAMPLE 3

250 g (2 mole) fluorosulfonyl isocyanate were dropped at room temperature while stirring over a period of 1 hour to a solution of 240 g (2.4 moles) i-propenyl acetate in 500 ml di-isopropyl ether. After a further 30 minutes the solution was added while cooling to 2,000 ml 4N methanolic potassium hydroxide solution. After suction filtration, 280 g (70% of theory, calculated on isocyanate) of the potassium salt of 6-methyl-3,4-dihydro-1,2,3-oxathiazin-4-one-2,2-dioxide were obtained.

The same result was obtained when the methanolic potassium hydroxide solution was added to the reaction mixture cooled to 5° – 10° C and stirring was continued for a further 30 minutes.

EXAMPLE 4

24.0 g (0.2 mole) fluorosulfonyl isocyanate and 22.0 g (0.22 mole) i-propenyl acetate were diluted to 50 ml each with methylene chloride. The solutions obtained were dropped into a reaction flask while stirring over a period of 30 minutes, the internal temperature in the flask being maintained at +20° C. While cooling with ice, 150 ml 4N methanolic potassium methylate solution were added dropwise to the reaction mixture whereby a crystalline product separated. By suction filtration 30 g of the potassium salt of 6-methyl-3,4-dihydro-1,2,3-oxathiazin-4-one-2,2,-dioxide were obtained, corresponding to a yield of 75% of the theory, calculated on the isocyanate used.

EXAMPLE 5

24 g (0.2 mole) fluorosulfonyl isocyanate were added dropwise while stirring at +5° C to 50 g (0.5 mole) i-propenyl acetate. After a further 30 minutes the unreacted i-propenyl acetate was distilled off under reduced pressure and the partially crystalline residue was added, while stirring and cooling, to 20° – 30° C, to 150 ml 4N methanolic potassium hydroxide solution. After suction filtration of the precipitate, 26 g (65% of theory, calculated on isocyanate) of the potassium salt of 6-methyl-3,4-dihydro-1,2,3-oxathiazin-4-one-2,2-dioxide were obtained.

EXAMPLE 6

6 g (0.025 mole) $\beta$-acetoxy-crotonic acid amide-N-sulfochloride of Example 1 were dissolved in 50 ml anhydrous methylene chloride, the solution was saturated with hydrogen chloride at 30° C and stirred for 4 hours under hydrogen chloride. After cooling to −60° C, 3.5 g (70% of theory) of acetoacetamide-n-sulfochloride crystallized out, which were characterized by IR spectrum and mixed melting point.

The product could be transformed in known manner into the oxathiazinone derivative of formula I.

What is claimed is:

1. A compound of the formula

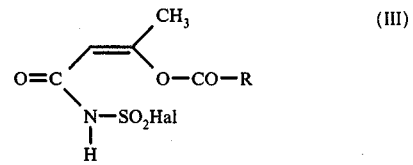

(III)

in which R represents an alkyl radical having from 1 to 4 carbon atoms and Hal stands for fluorine or chlorine.

2. A compound as claimed in claim 1 which is $\beta$-acetoxy-crotonic acid amide-N-sulfofluoride.

3. A compound as claimed in claim 1 which is $\beta$-acetoxy-crotonic acid amide-N-sulfochloride.

4. A process for the manufacture of a compound as defined in claim 1, which comprises reacting at a temperature of from −40° to +20° C an i-propenyl-alkanoic acid ester of the formula

(IV)

with an isocyanate of the formula $$O=C=N-SO_2Hal \quad (V)$$

in which R and Hal have the same meaning as in claim 1, and isolating the compound of formula III.

5. The process as claimed in claim 4, wherein the reaction is carried out with the addition of an inert aprotic solvent or diluent and the reaction product is isolated from the solvent or diluent used.

6. The process as claimed in claim 4, wherein the reaction is carried out at a temperature in the range of from −30° to +10° C.

7. The process as claimed in claim 4, wherein reaction components IV and V are used in stoichiometric amounts or one of them is used in an excess of up to 10%.

8. The process of claim 4, wherein i-propenyl acetate is reacted with fluorosulfonyl isocyanate.

9. The process of claim 4, wherein i-propenyl acetate is reacted with chlorosulfonyl isocyanate.

* * * * *